US00PP16030P2

(12) United States Plant Patent
Meilland

(10) Patent No.: US PP16,030 P2
(45) Date of Patent: Oct. 11, 2005

(54) GROUND COVER ROSE PLANT NAMED 'MEIRAMECA'

(50) Latin Name: *Rosa hybrida*
Varietal Denomination: Meirameca

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 36 days.

(21) Appl. No.: 10/405,634

(22) Filed: Apr. 3, 2003

Related U.S. Application Data

(63) Continuation of application No. 09/698,269, filed on Jan. 8, 2001, now abandoned.

(51) Int. Cl.[7] ..... A01H 5/00
(52) U.S. Cl. ..... Plt./107
(58) Field of Search ..... Plt./107, 114, 109

(56) References Cited

PUBLICATIONS

Saxton's Cottage and Farm Library. The American Rose Culturist; Being a Practical Treatise on the Propagation, Cultivation, and Management of The Rose. A.O. Moore, Agricultural Book Publisher, 1859. pp. 45–60.*

Webster's Ninth New Collegiate Dictionary. 1990. p. 213.*

UPOV–ROM GTITM, Plant Variety Database, 2003/06, GTI Jouve Retrieval Software, Citation for *Rosa* 'Meirameca'.*

Protection Des Obtentions Vegetales, Bulletin Officiel du Comité de la Protection des Obtentions Végétales, No. 4, cover page and pp. 124, 133, 136, 143 (1999).

* cited by examiner

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct variety of ground cover rose plant (i.e., garden rose plant) is provided which forms in abundance attractive semi-double blossoms that are pink in coloration. The vegetation is vigorous and the growth habit is creeping. Attractive decorative medium green glossy foliage is formed. Excellent disease resistance particularly with respect to Blackspot and Powdery Mildew is exhibited. The new variety grows very well on its own roots following asexual reproduction by cuttings. Attractive ornamentation in the landscape is provided.

1 Drawing Sheet

Figures 1, 2, 3, 4, 5, 6, 7, 8, 9, 10, 11, 12, 13, 14, 15, 16:
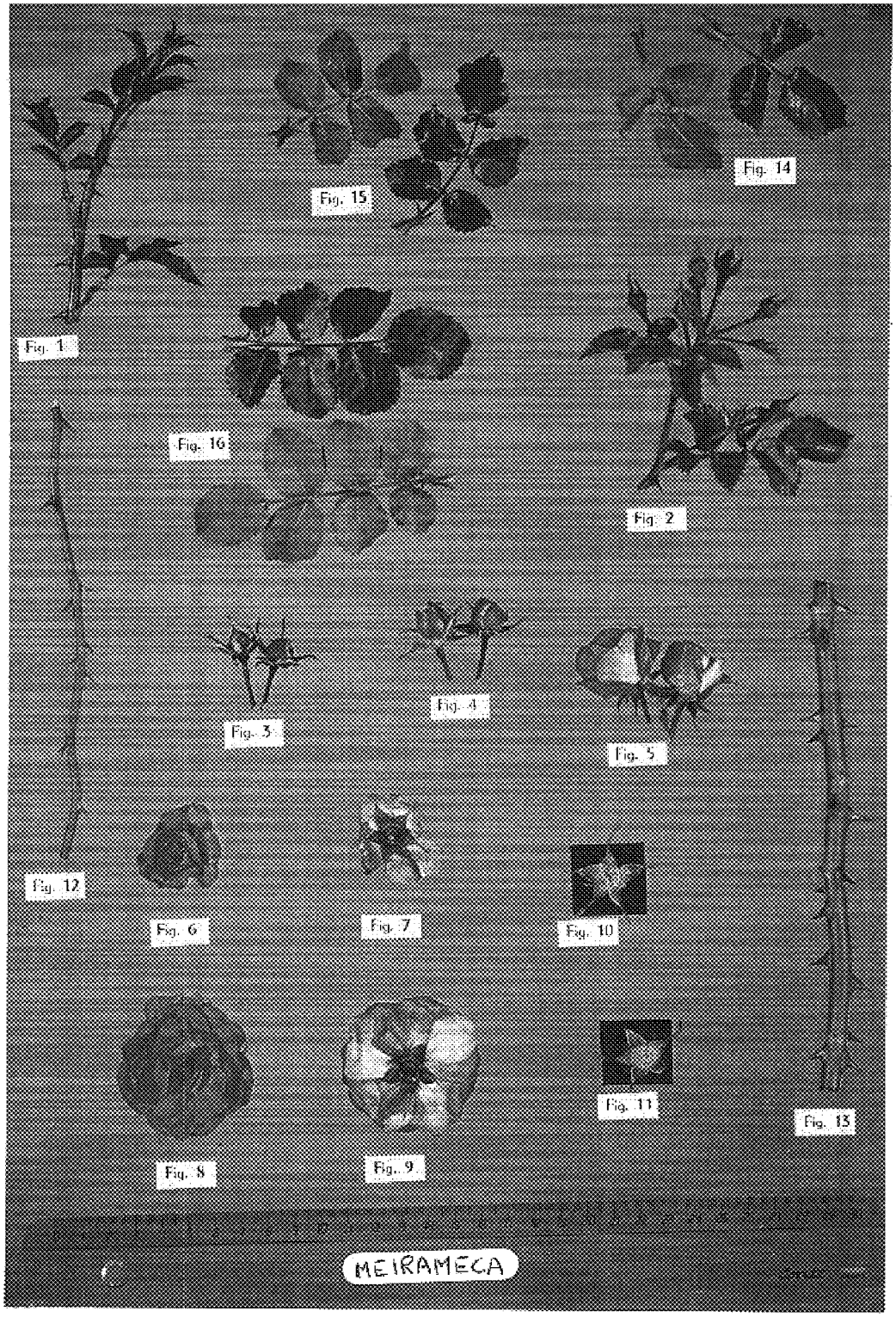

Botanical/commercial classification: *Rosa hybrida*/ Ground Cover Rose.
Varietal denomination: 'Meirameca'.

SUMMARY OF THE INVENTION

The new variety of *Rosa hybrida* Ground Cover rose plant of the present invention was created by artificial pollination wherein two parents were crossed which previously had been studied in the hope that they would contribute the desired characteristics. The female parent (i.e., the seed parent) of the new variety was the 'Noatraum' variety (U.S. Plant Pat. No. 7,282). The male parent (i.e., the pollen parent) of the new variety was the product of the cross between the 'Meibonrib' variety (U.S. Plant Pat. No. 9,469) and the 'Korimo' variety (non-patented in the United States). The 'Noatraum' parent variety sometimes is known as the 'Flower Carpet' variety. The parentage of the new variety can be summarized as follows:

'Noatraum'×('Meibonrib'×'Korimo').

The seeds resulting from the above pollination were sown and small plants were obtained which were physically and biologically different from each other. Selective study resulted in the identification of a single plant of the new variety.

It was found that the new variety of ground cover rose plant of the present invention possesses the following combination of characteristics:

(a) abundantly forms attractive semi-double blossoms that are pink in coloration,
(b) exhibits a creeping growth habit,
(c) forms vigorous vegetation,
(d) forms decorative medium green glossy foliage,
(e) propagates well by cuttings, and
(f) exhibits excellent disease resistance particularly with respect to Blackspot and Powdery Mildew.

The new variety well meets the needs of the horticultural industry. It can be grown to advantage as attractive ornamentation in parks, gardens, public areas, and residential landscapes. Accordingly, it is particularly well suited for growing in the landscape. The pink blossoms contrast nicely with the medium green glossy foliage.

The new variety of the present invention can be readily distinguished from its ancestors. More specifically, the 'Noatraum' variety forms blossoms that are more salmon in coloration and possess only approximately 15 petals, and the 'Meibonrib' variety forms strongly fragrant blossoms that are red-purple in coloration with lighter centers.

The new variety also can be readily distinguished from the related known 'TANydor' (non-patented in the United States) and 'KORsilan' (non-patented in the United States) varieties. More specifically, the 'TANydor' and 'KORsilan' varieties each form blossoms that display a darker coloration.

The characteristics of the new variety have been found to be homogeneous and stable and are strictly transmissible by asexual propagation at Le Cannet des Maures, France, such as budding, grafting, and cuttage from one generation to another. The plant propagates well and grows very well on its own roots when propagated from cuttings.

The new variety has been named the 'Meirameca' variety.

BRIEF DESCRIPTION OF THE PHOTOGRAPH

The accompanying photograph shows, as nearly true as it is reasonably possible to make the same in a color illustration of this character, typical specimens of the plant and plant parts of the new variety. The rose plants of the new variety illustrated herein were one year of age and were grown outdoors during June on their own roots at LeCannet-des-Maures, Var, France. Dimensions in centimeters are indicated at the bottom of the photograph.

FIG. 1—illustrates a specimen of a young shoot;

FIG. 2—illustrates specimens of floral buds before the opening of the sepals;

FIG. 3—illustrates specimens of floral buds at the opening of the sepals;

FIG. 4—illustrates specimens of floral buds at the opening of the petals;

FIG. 5—illustrates specimens of flowers in the course of opening;

FIG. 6—illustrates specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface and under surface;

FIG. 15—illustrates specimens of leaves with five leaflets—plan view—upper surface and under surface; and FIG. 16—illustrates specimens of leaves with seven leaflets—plan view—upper surface and under surface.

DETAILED DESCRIPTION

The chart used in the identification of colors is that of The Royal Horticultural Society (R.H.S. Colour Chart). The terminology which precedes reference to the chart has been added to indicate the corresponding color in more common terms. The description is based on one year-old specimens of the new variety during September while grown outdoors on their own roots at LeCannet-des-Maures, Var, France.

Class: Ground Cover (Garden Rose).

Plant:

*Height.*—Approximately 50 to 60 cm on average at the end of the growing season.

*Width.*—Approximately 120 to 130 cm on average at the end of the growing season.

*Habit.*—Creeping ground cover.

Branches:

*Color.*—Young stems: Very light green, near Yellow-Green Group 144B, suffused with reddish coloration. Adult wood: Near Yellow-Green Group 146C. Texture: Smooth with some prickles.

*Thorns.*—Size: Medium, and approximately 0.9 cm in length. Quantity: Moderately numerous. Color: Near Greyed-Red Group 180C when immature, and near Greyed-Orange Group 171D on adult wood.

Leaves:

*Stipules.*—Adnate, pectinate, smooth on the upper surface, pubescent on the under surface, and rather broad. The length commonly is approximately 1.7 cm on average and with width commonly is approximately 0.5 cm on average. The coloration is near Yellow-Green Group 146A and 146B on the upper surface, and near Yellow-Green Group 146B on the under surface.

*Petioles.*—Upper surface: Slightly glandular. Under surface: With a few prickles. Length: Approximately 1 cm on average. Diameter: Approximately 1 to 1.2 mm on average. Color: Near Yellow-Green Group 147A on the upper surface and near Yellow-Green Group 147B on the under surface.

*Leaflets.*—Number: 3, 5, and 7. Shape: Oval. Apex: Acuminate. Base: Rounded. Serration: Regular. Texture: Smooth and lustrous. Overall appearance: Dense, medium green in coloration, and glossy. Color (young foliage): Upper surface: Near Yellow-Green Group 146B with anthocyanin coloration near Red-Purple Group 166A. Under surface: Near Yellow-Green Group 146C with anthocyanin coloration near red-Purple Group 166A. Color (adult foliage): Upper surface: Near Yellow-Green Group 147A. Under surface: Near Yellow-Green Group 147B.

Inflorescence:

*Number of flowers.*—Commonly approximately 6 to 15 and sometimes more blooms per floral stem.

*Peduncle.*—Small, rigid, smooth, near Yellow-Green Group 146B and widely suffused with Greyed-Orange Group 166A in coloration, approximately 1.5 to 2 cm in length on average, and approximately 1 to 1.2 mm in diameter on average.

*Sepals.*—Upper surface: Near Greyed-Green Group 191C and suffused with Grey-Brown Group 166A. Under surface: Near Yellow-Green Group 146B and suffused with Greyed-Orange Group 166A. Configuration: The apex is lanceolate pointed and the base is linear, and commonly are lacking in foliaceous appendages. Texture: Tomentose on the upper surface and smooth on the under surface. Size: Commonly approximately 2.2 cm in length on average, and approximately 0.8 cm in width on average.

*Buds.*—Shape: Globular. Size: Small. Length: Approximately 1 cm. Color (when opening): Upper surface: Spinal Red, Red Group 54B, and suffused with Claret Rose, Red Group 50A. Under surface: Red Group 55D and lightly suffused with Claret Rose, Red Group 50B.

*Flower.*—Form: Flattened, and semi-double with the petals arranged in whorls. Diameter: Approximately 5 cm on average. Petal configuration: The apex is rounded with slight undulation and the base is pointed. Petal size: Commonly approximately 2.2 cm in length on average and approximately 2.4 cm in width on average. Petal number: Approximately 24 to 28 on average. Color (when opening begins): Upper surface: Spinal Red, near Red Group 54B, and suffused with Claret Rose, Red Group 50A. Under surface: Near Red Group 55D and lightly suffused with Claret Rose, Red Group 50B. Color (when blooming): Upper surface: Spinal Red, near Red Group 54A, and suffused with Claret Rose, Red Group 50A. Under surface: Spinal Red, near Red Group 54B. Color (at end of blooming): Upper surface: Spinal Red, near Red Group 54A, and suffused with Claret Rose, Red Group 50A. Under surface: Spinal Red, near Red Group 54B. Basal petal spot: White, near White Group 155A, on both surfaces. Petaloids: None observed to date. Fragrance: None. Lasting quality: Very long on the plant with the blossoms commonly lasting approximately 10 days on the plant. Petal drop: The petals commonly detach cleanly. Stamen number: Approximately 85 on average. Anthers: Yellow-orange, near Yellow-Orange Group 15A, in coloration, and approximately 1 to 1.5 mm in size on average. Filaments: Yellow, near Yellow Group 4D, in coloration, and approximately 3 to 4 mm in length on average. Pistils: Approximately 23 on average. Stigmas: Greenish, near Yellow-Green Group 145C, in coloration. Styles: Greenish, near Yellow-Green Group 145C, in coloration, and approximately 4 mm in length on average. Receptacle: Smooth, reddish green, near Green Group 143B, in coloration, approximately 5 to 7 mm in size on average and in longitudinal section it is in the shape of a pear. Hips/seeds: None observed to date.

Development:

*Vegetation.*—Very strong.

*Blossoming.*—Very abundant.

*Resistance to diseases.*—Excellent, especially with respect to Blackspot and Powdery Mildew.

*Hardiness.*—Has withstood −15° C.

I claim:

1. A new and distinct variety of Ground Cover rose plant characterized by the following combination of characteristics:

(a) abundantly forms attractive semi-double blossoms that are pink in coloration, (b) exhibits a creeping growth habit, (c) forms vigorous vegetation, (d) forms decorative medium green glossy foliage, (e) propagates well by cuttings, and (f) exhibits excellent disease resistance particularly with respect to Blackspot and Powdery Mildew;

substantially as herein shown and described.

* * * * *

MEIRAMECA